United States Patent [19]

Lee et al.

[11] Patent Number: 4,729,957
[45] Date of Patent: Mar. 8, 1988

[54] PROCESS FOR MANUFACTURE OF L-ASPARAGINASE FROM ERWINIA CHRYSANTHEMI

[75] Inventors: Shwu-Maan Lee, Frederick; John T. Ross, Myersville; Marie H. Wroble, Mt. Airy, all of Md.

[73] Assignee: The United States of America as represented by the Department of Health and Human Services, Washington, D.C.

[21] Appl. No.: 916,796

[22] Filed: Oct. 8, 1986

Related U.S. Application Data

[63] Continuation-in-part of Ser. No. 808,729, Dec. 13, 1984, abandoned.

[51] Int. Cl.$^4$ ............................ C12N 9/82; C12R 1/18
[52] U.S. Cl. .................................... 435/229; 435/815; 435/847
[58] Field of Search ............................ 435/229, 815

[56] References Cited

U.S. PATENT DOCUMENTS

| | | | |
|---|---|---|---|
| 3,511,754 | 5/1970 | Berk et al. | 435/229 |
| 3,511,755 | 5/1970 | Ratych | 435/229 |
| 3,589,982 | 6/1971 | Peterson et al. | 435/229 |
| 3,597,323 | 8/1971 | Roberts | 435/229 |
| 3,660,238 | 5/1972 | Wade | 435/229 |
| 3,684,659 | 8/1972 | Bergmeyer et al. | 435/229 |
| 3,686,072 | 8/1972 | Herbert et al. | 435/229 |
| 3,783,102 | 1/1974 | Callow et al. | 435/229 |
| 3,843,445 | 10/1974 | Christie et al. | 435/229 |
| 4,473,646 | 9/1984 | Guy et al. | 435/229 |

OTHER PUBLICATIONS

Buck et al, J. Gen. Microbiol., vol. 65, p. i (1971).
Karube et al in Biotechnology and Bioengineering, vol. 20, pp. 1775–1783 (1978).
Mardashev et al in Chemical Abstracts, vol. 83, No. 1, p. 298, 3257p (1975).
Suzuki et al in Chemical Abstracts, vol. 97, No. 13, p. 234, 105968c (1982).
Karsakevich et al in Chemical Abstracts, vol. 88, No. 21, p. 220, 14800x (1978).

Primary Examiner—Lionel M. Shapiro
Attorney, Agent, or Firm—John S. Roberts, Jr.

[57] ABSTRACT

A process for the recovery and purification of L-asparaginase from *Erwinia chrysanthemi* is disclosed. The process involves the preparation of cellular acetone powder extract followed by either an ion exchange and affinity chromatography purification steps or by affinity chromatography alone. The column eluent is then dialyzed to produce substantially pure L-asparaginase.

7 Claims, No Drawings

PROCESS FOR MANUFACTURE OF L-ASPARAGINASE FROM ERWINIA CHRYSANTHEMI

The invention described herein was made in the course of work under a contract or award from the Department of Health and Human Services.

This application is a continuation in part of pending Ser. No. 808,729 filed Dec. 13, 1984, now abandoned.

This invention involves a process for the production of L-asparaginase from bacterial cell cultures of *Erwinia chrysanthemi* which involves a multi-step separation procedure highlighted by a dual chromatographic separation, one for ion exchange and then for affinity or a single chromatographic separation using affinity chromatography. The generalized process is set out below. The enzyme is used therapeutically to benefit the treatment of leukemia.

A process for the recovery and purification of L-asparaginase from *Erwinia chrysanthemi* is disclosed. The process, as shown in the flow diagram, involves sequential ion exchange chromatography and affinity chromatography purification steps or affinity chromatography by itself followed by a dialysis step in order to produce substantially pure L-asparaginase.

GENERAL DESCRIPTION

A process is described for the recovery and purification of gram quantities of a therapeutic enzyme, L-asparaginase from submerged cultures of *Erwinia chrysanthemi*. Briefly, cells from *Erwinia chrysanthemi* fermentation broth are harvested and washed. A cellular acetone powder is prepared and extracted with pH 9.5 borate buffer. After centrifugation and filtration to remove cell debris, the acetone powder extract is adjusted to pH 7.7 and adsorbed onto an agarose column, such as CM-Sepharose Fast Flow (Pharmacia). Sepharose Fast Flow is a cross-linked agarose gel containing 6% agarose. This column is a low acid type suitable for ion exchange purpose. In addition, there is a pre-column packed with cell debris remover modified cellulose. The enzyme is desorbed from the ion-exchange column at pH 9.0 and further purified by an affinity column, such as L-asparagine Sepharose CL-4B, which column is tailored to select or allow molecular components. This affinity column is neutral as to ion selectivity as contrasted with the ion exchange column above. CL-4B is a cross-linked agarose gel containing about 4% agarose. L-Asn Sepharose CL-4B is made by linking L-Asn to Sepharose CL-4B through an epoxyactivation procedure. After dialysis-concentration to remove buffer salt, the L-asparaginase enzyme is depyrogenated, formulated, sterile filled, and lyophilized as single-dose final product.

The ion exchange chromatography step can be eliminated and substituted with at least one affinity chromatography step(s) using L-Asn Sepharose Fast Flow. L-Asn Sepharose Fast Flow is made by linking L-Asn to Sepharose Fast Flow beads through an epoxy activation procedure.

BACKGROUND OF THE INVENTION

L-asparaginase (L-asparagine amidohydrolase) catalyzes the hydrolysis of L-asparagine (L-Asn) to L-aspartic acid and ammonia. Interest in this enzyme arose a few decades ago when it was discovered that the antilymphoma activity of whole guinea pig serum was due to the enzyme L-asparaginase. Most normal tissues synthesize L-asparagine in amounts sufficient for their metabolic needs. Certain neoplastic tissues, in particular, acute lymphoblastic leukemic cells, require an exogenous source of this amino acid. L-asparaginase, by enzymatically catalyzing the hydrolysis of asparagine to aspartic acid and ammonia, deprives these malignant cells of the asparagine available from extracellular fluid, resulting in cellular death. L-asparaginase produced from *Escherichia coli* has a tumor inhibitory effect and the enzyme isolated from *Erwinia chrysanthemi* is also pharmacologically active. Since the L-asparaginases from *E. coli* and *Erwinia chrysanthemi* possess different immunological specificities, the availability of both provides an important alternative therapy if a patient happens to develop hypersensitivity to one of the enzymes (a common phenomena associated with the administration of L-asparaginase).

The process used by the only known manufacturer includes alkali lysis, multiple ion-exchange adsorptions, ammonium sulfate precipitation, multiple dialysis-concentration steps, and ethanol crystallization [Buck, et al., *J. Gen. Microbiol.*, Vol. 65, page i (1971)]. The present invention is an improved process to produce Erwinia L-asparaginase in gram quantities for therapeutic use.

As shown in U.S. Pat. No. 3,511,754 Berk, et al, and U.S. Pat. No. 3,511,755 Ratych, et al, the use of acetone in the production of *E. coli*-derived L-asparaginase is known to practitioners of the art. Part of the difficulty of large-scale production of this enzyme lies in the purification process. The only major manufacturer of asparaginase purifies the enzyme by a process which includes alkali lysis, multiple ion-exchange adsorptions, ammonium sulfate precipitation, multiple dialysis-concentration steps, and ethanol crystallization [Buck, et al, *J. Gen. Microbiol.*, Vol. 65, page i (1971)]. On the other hand, the present invention discloses a method by which significant purification of asparaginase may be achieved by initial ion-exchange chromatography. The material eluted from the ion exchange column (the starting material for the affinity column) contains only one extra protein contaminant as compared to the product available in the market. This extra protein contaminant is successfully removed by affinity chromatography. Moreover, the same purification can be achieved using affinity chromatography by itself.

Furthermore, compared to the multiple purification and dialysis steps used by Buck, et al, the process of the present invention includes only one or two chromatographic steps and one dialysis step. The enzyme is eluted from the ion-exchange column with a change in the buffer pH rather than a change in ionic strength. The enzyme coming off the column is very concentrated and contains low salt, thus avoiding a dialysis-concentration step between the ion-exchange and affinity chromatographic steps.

SPECIFIC DISCLOSURE

In the process of the present invention, L-asparaginase is purified from submerged cultures of *Erwinia chrysanthemi*. See Examples 1–5 for detailed descriptions of the processes. In its essence, the process begins with harvesting and washing Erwinia cells using a plate and frame type filter press or centrifugation. A cellular acetone powder is prepared from the buffer washed cells by one or more treatments with acetone. The cellular acetone powder is then extracted to form an enzyme-rich extract. The cell extract is again filtered or centrifuged to remove cell debris and form a cell-free enzyme extract (see Examples 1 and 2). The cell-free extract is applied to an ion exchange column, enzyme-rich fractions are pooled, and then applied to an affinity column. Alternately, the cell-free extract can be applied to the affinity column without going through the ion exchange column. Sequential washing and elution of the affinity column produces an enzyme which is substantially pure.

In the following specific method, as has been stated ante, alternative materials to the ion exchange CM Sepharose Fast Flow and affinity chromatography L-Asn Sepharose CL-4B column may be utilized.

The critical steps of this process are the preparation of a cellular acetone powder extract and the purification of the cell-free extract by means of chromatography—an ion exchange column and an affinity column or through an affinity clumn. The following describes a preferred method of purification.

ION EXCHANGE COLUMN PURIFICATION

CM-Sepharose Fast Flow (an ion exchanger sold by Pharmacia) is suspended in water and packed in a 16 L column (Pharmacia, 37×15 cm) with compressed air pressure of 1 bar. Cell debris remover (CDR) modified cellulose is pre-equilibrated with 0.1M sodium phosphate buffer, pH 7.7, basket centrifuged to remove the buffer, and re-equilibrated twice with 5 mM sodium phosphate buffer, pH 7.7. The CDR is packed in a 16 L column with the same buffer containing 0.1% benzalkonium chloride as a preservative. Before being used for the production run, the CM column and the CDR pre-column are each washed with at least 2 bed volumes of 5 mM sodium phosphate buffer, pH 7.7, to remove preservatives. The two column sections are serially joined and the flow (upward for CM column and downward for the pre-column) is maintained with a peristatic pump. The acetone powder extract is adjusted to pH 7.7 and applied to the columns with a flow rate of 0.5 L/min, which is equivalent to a linear flow rate of 28 cm/h. The flow rate can be reduced if necessary during the run to keep the running pressure at or below 1 bar. Following loading, the CDR pre-column is detached and the CM column is extensively washed with the buffer until the effluent is devoid of protein. The enzyme is then eluted from the column with 10 mM glycine buffer, pH 9.0. The enzyme-rich fractions are pooled, adjusted to pH 7.5 with dilute HCl and applied to the L-Asn Sepharose CL-4B or L-Asn Sepharose Fast Flow affinity column.

AFFINITY CHROMATOGRAPHY PURIFICATION

The L-Asn Sepharose CL-4B is prepared using methods adapted from Sundberg and Porath [J. Chromatogr., Vol. 90, p. 87 (1974)]. Sepharose CL-4B (Pharmacia, 4 Kg) is activated by reaction with 4 L of 1,4-butanediol diglycidyl ether and 4 L of 0.6 N sodium hydroxide solution containing 8 g of sodium borohydride. The activation reaction is allowed to proceed at room temperature for 15 hours in a 50-L glass rotary evaporator. The activated gel is recovered by suction filtration, washed seven times with 150 L of water each time and coupled to L-Asn by reaction of the gel with L-Asn (2 Kg) in 0.5M sodium carbonate buffer (35 L, final pH 8.5). The coupling reaction is allowed to proceed at room temperature for 15 hours with slow rotation in the same rotary evaporator. After the coupling step, the gel is washed seven times with 150 L of water each time and stored in 0.02% sodium azide.

The gel is packed in a column and the column is washed with at least 2 bed volumes of 5 mM sodium phosphate buffer, pH 7.5, to remove preservatives. A linear flow rate of 34 cm/h is used, which is equivalent to 2.7 L/h. At the end of loading, the column is washed with at least 5 bed volumes of the same buffer, and the enzyme is eluted with 10 mM glycine buffer, pH 9.0. The enzyme-rich fractions are pooled, adjusted to pH 7 with dilute HCl, and frozen at $-20°$ C. for final processing.

The affinity column eluent pool is thawed at 2° to 8° C., concentrated using a 2 L ultrafiltration pressure cell with C-30 membrane (cellulosic membrane, 30,000 dalton nominal molecular weight cut-off), and dialyzed at least $10^8$-fold with depyrogenated water for 15 hours. The dialyzed-concentrated enzyme is transferred to a 200 mL ultrafiltration pressure cell and further concentrated to a minimum titer of 30,000 IU/mL. The dialyzed concentrattion is depyrogenated, formulated, sterile-filled and lyophilized as a single dose final product.

The overall purification factor achieved from the ion-exchange and affinity chromatography is about 46-fold, as shown in Table 1. Table 2 shows the purification of L-asparaginase using filtration and affinity chromatography.

Erwinia is a gram negative microorganism and as such the cell-free extract contains high quantities of endotoxins. As shown in Table 1, the endotoxin level drops from 11.5 ng/ml to 0.676 ng/mL through ion-exchange chromatography and further decreases to 0.45 ng/mL through affinity chromatography. When depyrogenated water is used in all chromatographic operations, the enzyme-rich affinity column eluent contains endotoxins in the range of 0.1 to 0.5 ng/mL.

Aluminum oxide gel has been demonstrated to be an effective endotoxin adsorbent for certain proteins. It also has been demonstrated to be effective for pyrogen removal from L-asparaginase. In order to determine optimum conditions for depyrogenation, concentration and pH effects were studied. Purified L-asparaginase (protein concentration 2.45 mg/mL) containing an endotoxin concentration of 17 ng/mL was treated with an equal volume of varying concentrations of aluminum oxide while varying pH. As shown in Table 3, aluminum oxide appeared to be equally effective for depyrogenation at pH 5, 6, and 7 at 1% and 0.5%. At pH 7, however, some protein loss occurred.

TABLE 1

| | Recovery and Purification of L-Asparaginase from *Erwinia chrysanthemi* Using Centrifugation and Ion Exchange | | | | | |
|---|---|---|---|---|---|---|
| Steps | Total activity[a] (IU) ×10$^{-6}$ | Total protein[b] (g) | Specific activity (IU/mg) | Endotoxin (ng/mL) | Purification (fold) | Recovery (%) |
| (1) Whole broth | 9.0 | N.D.[c] | N.D.[c] | N.D.[c] | N.D.[c] | 100 |

TABLE 1-continued

Recovery and Purification of L-Asparaginase from *Erwinia chrysanthemi* Using Centrifugation and Ion Exchange

| Steps | Total activity[a] (IU) ×10$^{-6}$ | Total protein[b] (g) | Specific activity (IU/mg) | Endotoxin (ng/mL) | Purification (fold) | Recovery (%) |
|---|---|---|---|---|---|---|
| (2) Cell cake | 7.0 | N.D.[c] | N.D.[c] | N.D.[c] | N.D.[c] | 78 |
| (3) Acetone powder (1st) | 5.8 | N.D.[c] | N.D.[c] | N.D.[c] | N.D.[c] | 64 |
| (4) Acetone powder (2nd) | 4.8 | N.D.[c] | N.D.[c] | N.D.[c] | N.D.[c] | 53 |
| (5) Acetone powder extract | 2.9 | 430 | 6.7 | 11,500 | 1 | 32 |
| (6) CM-Sepharose Fast Flow | 2.3 | 7.4 | 310 | 0.676 | 46 | 26 |
| (7) L-Asn Sepharose CL-4B | 2.1 | 6.8 | 310 | 0.45 | 46 | 23 |

[a]Determined by ammonia probe assay
[b]Determined by Bio-Rad dye binding assay
[c]Not determined

TABLE 2

Recovery and Purification of L-Asparaginase Using Filtration and Affinity Chromatography

| Steps | Enzyme Activity (I.U./mL) | Protein Concentration (mg/mL) | Volume (L) | Specific Activity (I.U./mg) | Total Activity (I.U.) 10$^{-6}$ | Total Protein (g) | Purification (fold) | Recovery (%) | Endotoxin (ng/mL) |
|---|---|---|---|---|---|---|---|---|---|
| (1) Whole broth | 42 | — | 880 | — | 37 | — | — | 100 | — |
| (2) Acetone powder extract | 15 | 0.32 | 1400 | 47 | 21 | 448 | 1.0 | 57 | — |
| (3) L-Asn Sepharose Fast Flow Affinity column (9 l) | 1300 | 3.3 | 10.5 | 394 | 14 | 35 | 8.4 | 38 | 1.34 |

TABLE 3

Dose and pH Effect of Aluminum Oxide Depyrogenation

| Aluminum oxide (%) | pH | Protein Concentration* After Treatment (mg/mL) | Endotoxin Level After Treatment (ng/mL) |
|---|---|---|---|
| 1 | 5 | 1.3 | <0.006 |
| 1 | 6 | 1.3 | <0.006 |
| 1 | 7 | 0.87 | <0.006 |
| 0.5 | 5 | 1.4 | <0.006 |
| 0.5 | 6 | 1.3 | <0.006 |
| 0.5 | 7 | 1.1 | <0.006 |

*Purified asparaginase (2.45 mg/mL) with endotoxin concentration 17 ng/mL was mixed with equal volumes of aluminum oxide solution at different percentages, which increased total volume to two fold. Protein concentration was expected to be 1.2 mg/mL after treatment, assuming protein was not adsorbed by aluminux oxide gel.

In this process, the cells were treated with acetone and the enzymes were recovered by borate extraction. The average step yield for acetone powder preparation was about 60% and for extraction was about 80%. The yields were slightly lower than the other methods reported (toluene-urea lysis: 85%, alkali lysis: 60–100%). Alkali lysis, in our experience, however, gave very poor yield (6%). Toluene-urea treatment, osmotic shock and mechanical fracture gave unsatisfactory results as well.

The use of the word chromatography is intended to include processes by which complex mixtures of molecules are separated by repeated partitionings between a flowing phase and a stationary phase. In ion exchange chromatography, a synthetic resin containing fixed charged groups attracts and binds charged substituents in a sample mixture. In affinity chromatography, proteins in a mixture are removed by exposing the mixture to a column containing a specific ligand for the protein. When the column is washed with buffer, the only protein(s) that remain on the column are those with a high affinity for the ligand.

The present invention also discloses the use of a filter press in the production of an enzyme-rich extract. Such filter presses are well known in the art of biomass separation and include flush-plate or plate-and-frame presses. See *Chemical Engineers Handbook*, Robert H. Perry and Cecil H. Chilton, eds., page 19–65 (1973).

EXAMPLE 1

A production-scale process was developed to purify a therapeutic enzyme, L-asparaginase from submerged cultures of *Erwinia chrysanthemi*. Cells from 880 L of fermentation broth were harvested and washed using a 208 sq. ft. plate and frame-type filter press. A cellular acetone powder was prepared from the washed cells by suspending the cells in acetone at 10° C., then the acetone powder was recovered using the filter press. After a second acetone treatment, the residual acetone was removed by washing the acetone powder in the filter press with 10 mM phosphate buffer (pH 7.0). The acetone powder was then extracted with 10 mM borate buffer at pH 9.5. The enzyme-rich borate extract was recovered by filtration through the filter press and clarified by in-line passage through a bag filter loaded with Cell Debris Remover. The filtrate was adjusted to about pH 7.5 and then filtered through a 1μ bag filter precoated with filter aid (Celite) followed by a sterile 0.22 u final filter.

EXAMPLE 2

Preparation of a cell extract: Cells were harvested from chilled whole cell broth (150 L) using two refrigerated vertical bowl centrifuges operating at 9,000 xg and a flow rate of 1 L/min. The 4 kg of wet cell paste recovered was resuspended in 150 L of 10 mM potassium phosphate buffer, pH 7.0, and mixed for 30 min. The washed cells were again recovered by centrifugation. Acetone powder was prepared by resuspending the cell paste in 150 L of anhydrous acetone at 10° C. and agitating for 30 min. To the mixture of acetone/cells was added 1.5 Kg of a fine diatomatious earth filter aid (Supercel, Johns-Manville Company), and the suspension was basket centrifuged using a 2 kg precoat of coarse filter aid (Celite type 545). The recovered solids (first acetone powder) were treated the same way a second time. This second acetone powder was extracted with 150 L of 10 mM sodium borate buffer, pH 9.5, for 40 min and the extract was clarified by basket centrifugation (1,100 xg). The enzyme-rich extract was adjusted to about pH 7.7, then serially filtered through a Celite precoated 1μ bag filter and a 0.45μ nominal hydrophilic cartridge filter.

EXAMPLE 3

The sterile cell-free acetone powder extract at about pH 7.5 (1400 L) was applied to an L-Asn Sepharose Fast Flow affinity column (25.2×18 cm, 9 L bed volume) at a flow rate of 80 L/h using a bag filter loaded with Cell Debris Remover as an in-line pre-filter. The affinity gel was prepared by coupling L-Asn at pH 9.0 to epoxy-activated Sepharose Fast Flow beads. After washing the column with at least 10 bed volumes of 5 mM sodium phosphate buffer, pH 7.5, the column was eluted with 10 mM glycine buffer at pH 9.0. A total of $14 \times 10^6$ IU (35 g protein) of purified enzyme was eluted from the column in 10.5 L volume. A 9-fold purification of enzyme with a 10,000-fold reduction of endotoxins was achieved with affinity chromatography. The eluted enzyme was determined to be greater than 90% pure when assayed by sodium dodecyl sulfate polyacrylamide gel electrophoresis.

EXAMPLE 5

Table 4 summarizes a typical final processing lot from the affinity column eluate pool to the sterile formulated enzyme. The overall yield of the product from fermentation broth to final formulated product as produced for this lot by this invention was 19%. See Table 4.

TABLE 4

L-Asparaginase Lot XX004B Final Processing

| Steps | Enzyme Activity (IU/mL)* | Total Volume (mL) | Total Activity (IU)-6 | Recovery (%) |
|---|---|---|---|---|
| (1) Affinity column pool | 2,610 | 1,000 | 2.61 | 100 |
| (2) Dialyzed concentrated enzyme | 54,600 | 46 | 2.51 | 96 |
| (3) Aluminum oxide treatment | 26,700 | 85 | 2.26 | 87 |
| (4) Diluted enzyme before formulation | 13,300 | 167 | 2.22 | 85 |
| (5) Formulated sterile filtered enzyme | 10,800 | 197 | 2.13 | 82 |

*Determined by Nessler reaction

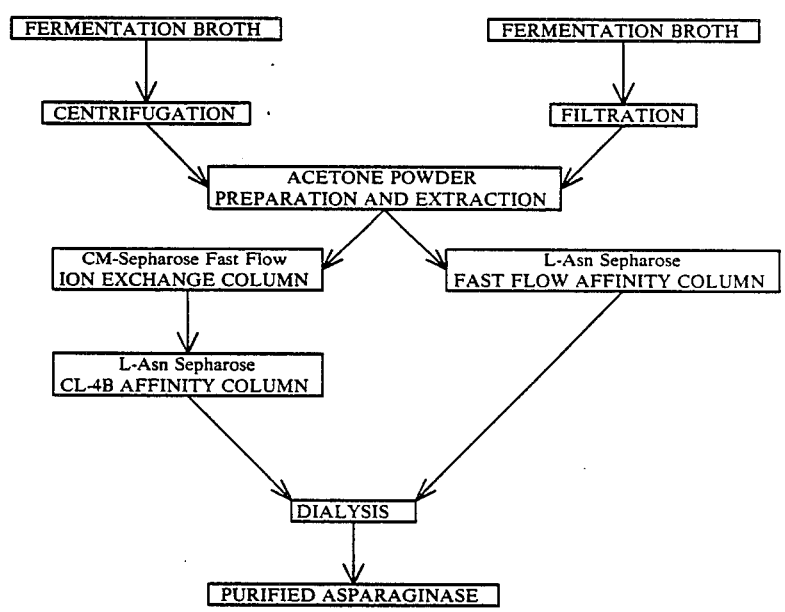

when assayed by sodium dodecyl sulfate polyacrylamide gel electrophoresis.

EXAMPLE 4

The cell-free acetone powder extract (150 L) at about pH 7.7 is adsorbed onto a 16 L CM-Sepharose Fast Flow column using a pre-column packed with Cell Debris Remover modified cellulose. The column was washed at pH 7.7, the enzyme was desorbed from the ion exchange column at pH 9.0 and further purified by an affinity column of L-Asparagine Sepharose at pH 7.5. After washing the column with at least 5 bed volumes of 5 mM phosphate buffer, pH 7.5, the column was eluted with 10 mM glycine buffer at pH 9.0. A total of 7 grams substantially purified enzyme was eluted from the column. A 46-fold purification of enzyme with 10,000-fold reduction of endotoxin was achieved. The

What is claimed is:
1. A process for purifying L-asparaginase from Erwina comprising the steps of:
 (1). Harvesting cells from both;
 (2). Permealizing the Erwina by mixing with acetone and passing acetone/cell mixture through a filter press at least once;
 (3). Rinsing the acetone/cell cake with buffer in the neutral pH range (pH 6.5-7.5) to remove acetone;
 (4). Rinsing cells with buffer in alkaline range;
 (5). Pass cells from step 4 through a cell press to extract the enzyme;
 (6). Clarify the enzyme containing fluid obtained in step 5 by in-line passage through filter bag loaded with Cell Debris Remover;

(7). Purifying the enzyme on an affinity chromatography column.

2. A process of claim 1 wherein the organism used is *Erwina Chrysanthemi*.

3. A process of claim 1 wherein step 2 is performed twice.

4. A process of claim 1 wherein the chromatography column is an ion-exchange column.

5. A process of claim 1 wherein the column is an affinity bead column.

6. A process of claim 5 wherein the heads are sepharose Fast Flow beads.

7. A process of claim 1 wherein the buffer of step 4 is 10 mM borate at pH 9.5.

* * * * *